United States Patent

McClure et al.

[11] Patent Number: 5,898,474
[45] Date of Patent: Apr. 27, 1999

[54] VISUAL FIELD TESTING METHOD AND APPARATUS

[76] Inventors: Richard J. McClure, 4981 September St., San Diego, Calif. 92110; R. Kemp Massengill, 15350 Via Molinero, Poway, Calif. 92064

[21] Appl. No.: 08/864,331

[22] Filed: May 28, 1997

Related U.S. Application Data

[63] Continuation of application No. 08/700,754, Jul. 31, 1996.
[51] Int. Cl.⁶ ........................................... A61B 3/02
[52] U.S. Cl. .................... 351/224; 351/246; 351/210
[58] Field of Search ................................ 351/222, 224, 351/226, 237, 239, 246, 209, 210

[56] References Cited

U.S. PATENT DOCUMENTS 5,461,435  10/1995  Rootzen et al. ...................... 351/224
5,649,061  7/1997  Smyth ................................. 351/210

Primary Examiner—Huy Mai
Attorney, Agent, or Firm—Gerald W. Spinks

[57] ABSTRACT

A method and apparatus are disclosed for using virtual reality for testing and quantifying visual information from the eye, the visual pathways, and the brain. Headgear configuration allows the patient to observe a field of view into which sequenced test stimuli are presented by an excitation device commanded by a computer. Interactive sensory feedback both to and from the patient enables computer-driven presentation and modulation of test stimuli to measure with precision such parameters as visual field performance, visual acuity, and color vision. Using the system allows the patient unprecedented freedom of movement of the head and body, thus minimizing or even eliminating the stress and fatigue common with conventional non-virtual reality visual field testing systems.

28 Claims, 1 Drawing Sheet

VISUAL FIELD TESTING METHOD AND APPARATUS

CROSS REFERENCE TO RELATED APPLICATIONS

This is a continuation patent application of co-pending U.S. patent application Ser. No. 08/700,754, filed on Jul. 31, 1996, pending and entitled "Visual Field Testing Method and Apparatus Using Virtual Reality".

FEDERALLY SPONSORED RESEARCH OR DEVELOPMENT

Not Applicable

BACKGROUND OF THE INVENTION

This invention relates to optical testing of the eye's sensitivity to various parameters of light, and in particular to visual field evaluation, using a virtual reality system.

In the field of medicine where disorders of the eye are treated, it is necessary to measure the sensitivity to light in various regions of the light-sensitive retina. So doing measures function, as well as quantifying disorders of the eye and the retina, the optic nerve, the optic chiasm, the visual pathways to the brain, and the brain itself. Visual field testing is mandatory for glaucoma diagnosis and treatment. Apparatus to measure the field of vision is used by ophthalmologists and optometrists for these purposes and is relatively complex in its various functions, some of which complexity tends to make the human patient become tired or lose attention to the test.

BRIEF SUMMARY OF THE INVENTION

The purpose of the presently-described method and apparatus for visual field testing is to allow the sensitivity of the visual field to be measured without the attendant stress of the patient, and yet to preserve accuracy. The means by which this is accomplished uses concepts and apparatus from virtual reality. Virtual reality is a term applied loosely to the experience of an individual when exposed to the appearance of surroundings which are presented by interactive apparatus for stimulation of the senses. The primary cues are usually visual, supplemented by audio, and the feedback to the apparatus is generally by physical movements of the individual experiencing the virtual reality (such as pressing a button or a switch, or speaking into a microphone).

The disclosed virtual reality visual field measuring method and apparatus uses a headmounted goggle or face mask unit to present visual and audio stimuli to a patient. The visual portion has both relatively fixed image information, and superimposed visual areas, which may vary in time, place, color, and intensity. These stimuli are generated and controlled by software in an associated computer, which receives interactive feedback stimuli from the patient. Such stimuli include, but are not limited to, direction of gaze sensing, eyelid movement and blinking, audio, and hand pressure signals on cue.

Content of the software is dictated by the need to provide technically acceptable protocols. Such protocols provide for examining wide and narrow fields of view, selected areas, such as the blind spot or the fovea, and measurements of thresholds for sensitivity to light intensity, or, if desired, color. These are usually done for one eye at a time, each looking at the same, or similar, field of views.

Active feedback sensing alerts the system to patient loss of attention in general, or loss of fixation in particular, for notation and reiteration of test stimuli. In the presently-described method and apparatus, provision is also made for reiteration of individual test points when a result is found to be inconsistent with a predetermined norm, or when lack of concentration or poor cooperation becomes evident, with appropriate care taken to provide no leading cues which may cause false positive or false negative responses. The software allows optional restful imagery to be provided in the "background," in addition to a conventional, uniform featureless field. The imagery in various quadrants/areas may be patterns, or low-contrast images, and may move quickly or slowly, and may have intensity, color, or temporal modulation. The intensity, color, location, and duration of the superimposed test points are displayed by conventional electronic means, such as are now used in image presentations. Such means include cathode-ray tube, electroluminescent, liquid crystal, and gas discharge panels. A hard-copy printout documenting patient responses is provided for the physician's records.

Another object of the present system is to provide relief from the stress of being required to concentrate, without head movement, one's gaze at a fixed location, as is the case with conventional visual field testers. The gaze sensor may be multi-element, so as to allow the gaze to be detected in a small solid angular range and, within this range, the effective fixation will be deemed to be maintained. The software may include an interest-fixation icon which encourages the gaze to trace its motion within the allowed solid angle, thus avoiding fixation fatigue. The software keeps track of the location of the test point frame of reference within that solid angle of displacement, so as to provide accurate mapping of test data on the field of view presented to the retina.

In addition to visual field testing, it is certainly within the scope of this invention to provide other virtual reality computer-driven, interactive testing capability, such as for visual acuity and color testing.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
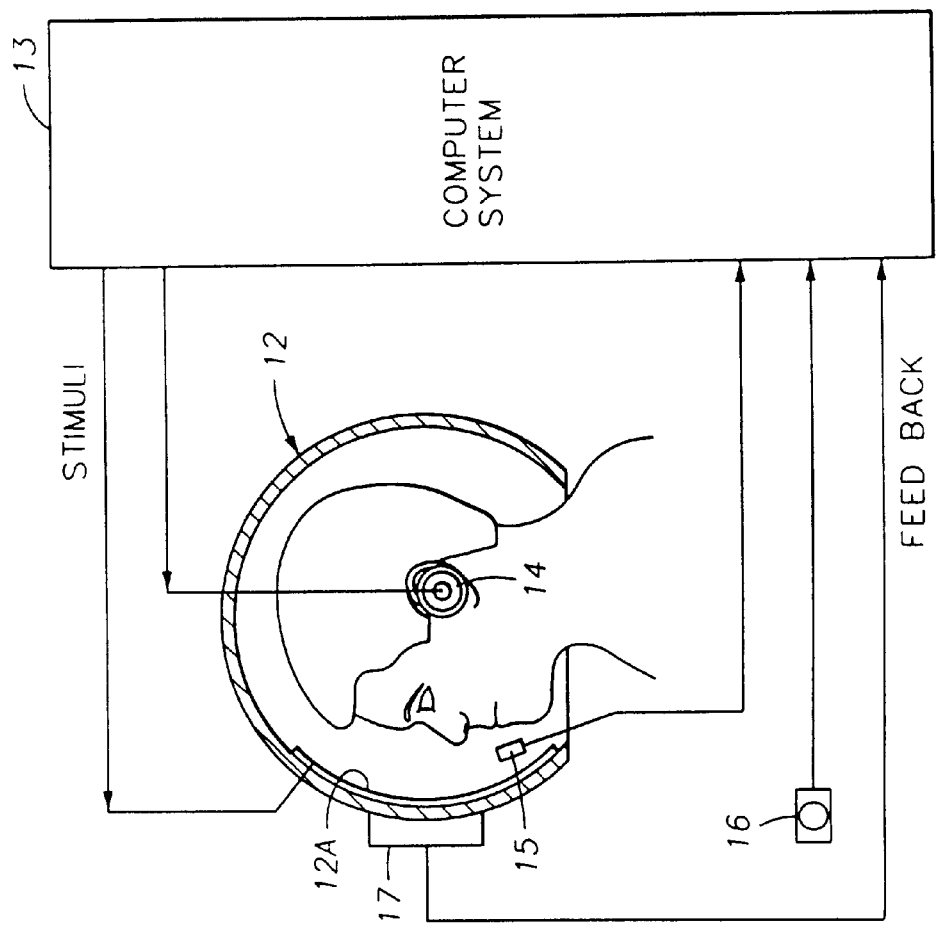
FIG. 1 is a schematic view of the apparatus of the present invention.

FIG. 1 shows a schematic of the virtual reality visual field testing system 5 of the present invention, in which a head-gear assembly 12 is connected to a computer 13, which delivers a visual signal to a head-gear display screen 12(a), and an audio signal to a head-gear earphone 14.

The head-mounted visual display apparatus, head-gear 12, which remains in a fixed spatial relationship to the patient's head during testing of the visual field, is adjustable to suit the individual patient, and is mounted on the patient's head by conventional means. The screen display 12(a) is part of the head-gear 12 and encompasses the maximum field of view required. The head-gear 12 is provided with an integral microphone 15 and a speaker or earphone 14, for audio communication and feedback, and a multi-element gaze-aim sensor array 17. The microphone 15 provides feedback audio response to the computer 13. The head-gear assembly 12 is connected, by appropriate means, to the computer 13 which provides the necessary visual and audio stimuli for the patient, and which receives the feedback responses to enable interactive functioning of the system. A hand-operated switch 16 is incorporated to provide feedback to the computer 13, and the gaze sensor 17, mounted in the direction of gaze, provides optical gaze direction feedback to the computer 13.

Figure 2A:
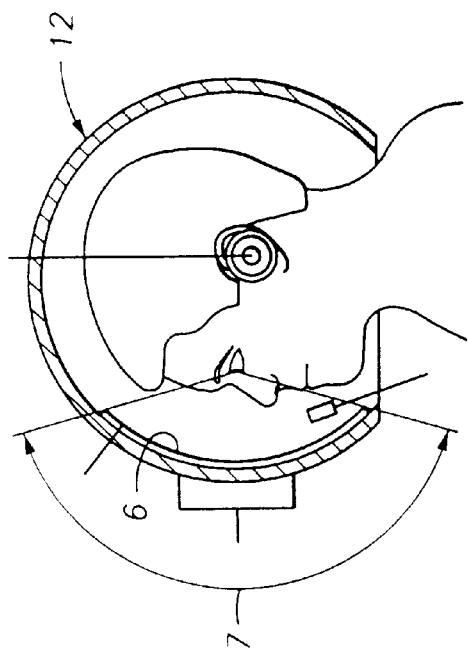
FIG. 2(a) is a schematic view of the apparatus of FIG. 1 measuring a vertical angular field of view.

FIG. 2(a) shows, by dashed line 6, a vertical image surface covering an angular field of view 7 on the screen display 12(a).

Figure 2B:
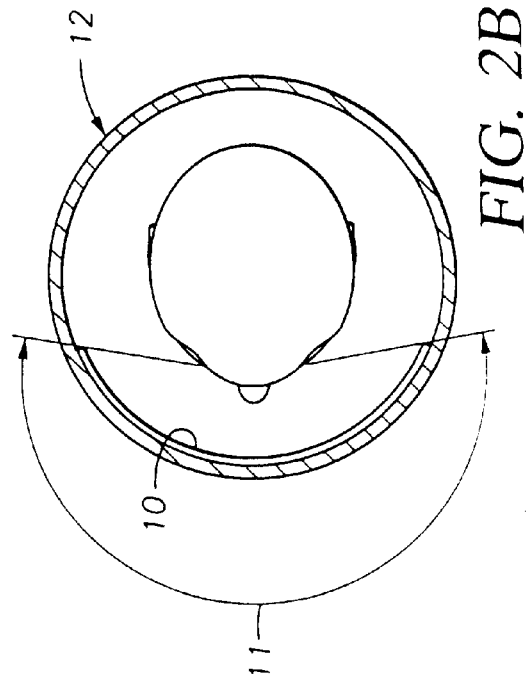
FIG. 2(b) is a schematic view of the apparatus of FIG. 1 measuring a horizontal angular field of view.

FIG. 2(b) shows, by dashed line 10, a horizontal image surface covering an angular field of view 11 on the screen display 12(a).

An element of the virtual reality visual field testing system 5 is that it allows the patient the freedom to shift his/her gaze, while in the test mode, without disruption of the process, thus relieving one of the causes of patient stress. Another feature provided is the ability to modulate the background scene brightness, contrast, color, optical stimulus size and detail, and duration of the test stimuli, all of which serve to relieve fatigue of the patient. Of paramount significance is that the patient may move around bodily, since the head gear 12 is portable and, in addition, electrical interfaces to the computer 13 may be wireless.

In addition to a vastly more patient-friendly and portable test setting, a further significant advantage of the presently-described method and apparatus is that background light intensity and other parameters can be easily calibrated to predetermined settings, thus eliminating the requirement mandated by conventional visual field testers to calibrate these parameters for the entire room. For instance, the fact that room brightness can vary almost imperceptibly, but yet significantly, from day to day in conventional visual field testing situations creates built-in unreliability of the test data received from the patient.

Furthermore, feelings of anxiety frequently displayed by patients undergoing conventional visual field testing in which first one eye and then the fellow eye is covered with an occluder patch can be eliminated in the preferred embodiment, since both eyes can be tested simultaneously, or separately and independently, through the use of individual eye goggles, or an appropriate face mask, to provide gaze separation.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A visual field testing apparatus, comprising:
    a frame, said frame being adapted to mount in a substantially motionless relationship to the head of a patient, while allowing the head to move;
    an electronic image display device mounted to said frame, said display device being constructed and positioned to display an electronic image encompassing the visual field of at least one eye of the patient wearing said frame;
    a gaze sensing device adapted to sense the orientation of at least one eye of the patient wearing said frame and to generate a gaze orientation signal;
    a response sensing device adapted to sense a patient's response to a visual stimulus and to generate a response signal; and
    a computer, said computer being connected to said display device to generate said electronic image, said computer being connected to said gaze sensing device to receive said gaze orientation signal, said computer being connected to said response sensing device to receive said response signal, and said computer being capable of measuring said gaze orientation signal and said response signal and calculating at least one characteristic of the visual field of the patient.

2. A visual field testing apparatus as recited in claim 1, wherein:
    said electronic image display device is constructed and positioned to display an electronic image encompassing the visual field of both eyes of a patient wearing said frame; and
    said gaze sensing device is adapted to sense the orientations of both eyes of a patient wearing said frame and to generate a gaze orientation signal for each eye.

3. A visual field testing apparatus as recited in claim 1, wherein said computer is programmable to vary at least one characteristic of said electronic image.

4. A visual field testing apparatus as recited in claim 3, wherein said characteristic is location.

5. A visual field testing apparatus as recited in claim 3, wherein said characteristic is shape.

6. A visual field testing apparatus as recited in claim 3, wherein said characteristic is size.

7. A visual field testing apparatus as recited in claim 3, wherein said characteristic is color.

8. A visual field testing apparatus as recited in claim 3, wherein said characteristic is color intensity.

9. A visual field testing apparatus as recited in claim 3, wherein said characteristic is brightness.

10. A visual field testing apparatus as recited in claim 3, wherein said characteristic is residence time.

11. A visual field testing apparatus as recited in claim 1, wherein said electronic image includes a background upon which another feature is displayed.

12. A visual field testing apparatus as recited in claim 1, wherein said response sensing device comprises a switch manipulated by the patient.

13. A visual field testing apparatus as recited in claim 1, wherein said response sensing device comprises a motion detector.

14. A visual field testing apparatus as recited in claim 1, wherein said response sensing device comprises a sound detector.

15. A visual field testing apparatus as recited in claim 1, wherein said response sensing device comprises a gaze sensor.

16. A visual field testing apparatus as recited in claim 1, wherein said computer is programmable to analyze said signals to recognize faulty data resulting from inaccurate patient responses.

17. A visual field testing apparatus as recited in claim 1, wherein said computer is programmable to shift said electronic image to maintain said image in a desired location relative to said gaze orientation of the patient.

18. A visual field testing apparatus as recited in claim 1, wherein said visual field characteristic is the nature and extent of the peripheral field of vision of the patient.

19. A visual field testing apparatus as recited in claim 1, wherein said visual field characteristic is the nature and extent of the color vision of the patient.

20. A visual field testing apparatus as recited in claim 1, wherein said visual field characteristic is the nature and extent of the visual acuity of the patient.

21. A visual field testing apparatus as recited in claim 1, wherein said display device comprises a cathode ray tube.

22. A visual field testing apparatus as recited in claim 1, wherein said display device comprises an electroluminescent display.

23. A visual field testing apparatus as recited in claim 1, wherein said display device comprises a liquid crystal display.

24. A visual field testing apparatus as recited in claim 1, wherein said display device comprises a gas discharge display.

25. A method for measuring at least one characteristic of the visual field of a patient, comprising:

mounting a virtual reality apparatus in a substantially motionless relationship to the head of a patient, while allowing the head to move, said virtual reality apparatus having an electronic image display device, a gaze sensing device, a response sensing device, and said virtual reality apparatus being connected to a computer;

displaying an electronic image generated by said computer, said image encompassing the visual field of at least one eye of the patient;

sensing the orientation of at least one eye of the patient and generating a gaze orientation signal;

sensing the patient's response to said electronic image and generating a response signal;

receiving said gaze orientation signal and said response signal with said computer and calculating at least one characteristic of the visual field of the patient.

26. A method as recited in claim 25, further comprising varying at least one characteristic of said electronic image.

27. A method as recited in claim 25, further comprising analyzing said signals to recognize faulty data resulting from inaccurate patient responses.

28. A method as recited in claim 25, further comprising shifting said electronic image to maintain said image in a desired location relative to said gaze orientation of the patient.

* * * * *